United States Patent
Arnoux et al.

[11] Patent Number: 5,864,911
[45] Date of Patent: Feb. 2, 1999

[54] TOOTHBRUSH WITH A DUAL ROTARY BRUSHING SYSTEM

[75] Inventors: Patrick Arnoux, 156, Avenue Des Chartreux, 13004 Marseille; Jean-Christophe Ferrer, 25 Av. Fontsainte, Les Fauvettes, 13600 La Ciotat, both of France

[73] Assignees: Patrick Arnoux, Marseille; Jean-Christophe Ferrer, La Ciotat; Elisabeth Deleforges, Paris, all of France

[21] Appl. No.: 635,899
[22] PCT Filed: Oct. 21, 1994
[86] PCT No.: PCT/FR94/01231
  § 371 Date: Sep. 27, 1996
  § 102(e) Date: Sep. 27, 1996
[87] PCT Pub. No.: WO95/11636
  PCT Pub. Date: May 4, 1995

[30] Foreign Application Priority Data

Oct. 26, 1993 [FR] France ................... 93/13031
Sep. 20, 1994 [FR] France ................... 94/11538

[51] Int. Cl.⁶ ................................................. A46B 13/02
[52] U.S. Cl. ......................................................... 15/23
[58] Field of Search ........................................ 15/23, 24

[56] References Cited

U.S. PATENT DOCUMENTS

| | | |
|---|---|---|
| 2,628,377 | 2/1953 | Cockriel ................... 15/23 |
| 2,758,326 | 8/1956 | Keely ...................... 15/23 |
| 3,605,154 | 9/1971 | Dawkins ................... 15/24 |
| 4,060,870 | 12/1977 | Cannarella . |
| 4,313,237 | 2/1982 | Smith . |
| 4,377,877 | 3/1983 | O'Rourke . |
| 4,538,315 | 9/1985 | Barth ...................... 15/23 |
| 5,173,983 | 12/1992 | Le . |
| 5,177,827 | 1/1993 | Ellison . |

FOREIGN PATENT DOCUMENTS

| | | |
|---|---|---|
| 0103959 | 3/1984 | European Pat. Off. ............ 15/23 |
| 0488971 | 6/1992 | European Pat. Off. . |
| 110160 | 4/1900 | Germany .................... 15/23 |
| 3306969 | 5/1984 | Germany .................... 15/23 |
| 4207686 | 9/1993 | Germany . |
| 644256 | 7/1984 | Switzerland . |
| 1118699 | 7/1968 | United Kingdom ............ 15/23 |

*Primary Examiner*—Randall E. Chin
*Attorney, Agent, or Firm*—Ladas & Parry

[57] ABSTRACT

The present invention provides a mechanical toothbrush with a dual rotary brushing system and comprising a handle-forming body and a head fixed to the handle, which head is provided with two adjacent contra-rotating brushes of cylindrical shape and having substantially parallel axes. Each of the two brushes is driven by a flexible shaft situated in the head and supported, at least at its distal end, by a respective bearing mounted on a support that enables the two brushes to move apart one away from the other, then urging the brushes towards the other by a return effect.

12 Claims, 2 Drawing Sheets

TOOTHBRUSH WITH A DUAL ROTARY BRUSHING SYSTEM

The present invention relates to a toothbrush with a dual rotary brushing system.

In general manner it relates to the fields of mouth hygiene and dental care, in particular for humans, but it may readily be adapted to veterinary use.

BACKGROUND OF THE INVENTION

For a long time specialists have been agreed that in order to be really effective, teeth must be brushed from the gum towards the end of the tooth, i.e. downwards for the top jaw and upwards for the bottom jaw.

There presently exist many types of electric toothbrush, with vibrating, reciprocating, or rotary motion. For example, European patent EP 0 488 971 describes an electric toothbrush having two contrarotating brushes disposed to act on the same side of the dental arch. Under such circumstances, it is clear that although one of the brushes is always operating in the proper direction, the other one is necessarily acting in the wrong direction.

None of those devices can guarantee that brushing will always take place in the best direction, unless an automatic system is incorporated therein for reversing the direction of rotation as a function of the position of the device in the mouth, and such a system would be complex, expensive, and generally unreliable.

To mitigate the above drawbacks, tooth brushing devices are nevertheless known which include cylindrical brushes having parallel axes that are rotated in opposite directions, enabling the teeth that are to be cleaned to be inserted between them so that each side of a tooth is brushed in the root-to-end direction: by way of example of a device of this category, in which the present invention belongs, mention may be made of patent application FR 2 489 120 published on Mar. 5, 1982 which describes such a brushing device in which the cylindrical brushes are spaced apart by a constant distance greater than the maximum width of a tooth (about 5 millimeters as mentioned in the application), and are free at their distal ends (i.e. their ends remote from the handle containing the system for applying rotary drive to said brushes via their opposite ends). Devices of the same type also include patent CH 644256 published on Jul. 31, 1984, in which the brushes are provided with shafts of conical section and made of synthetic material whose resilience enables a certain amount of pressure to be obtained against the teeth that are encompassed between them. To avoid any risk of obtaining an effect that is the opposite of the intended result, devices of that type necessarily include means for controlling the direction of brushing, either by reversing the direction of rotation of the drive motor, or else by means of angled couplings imposing a determined position on the brushes relative to the dental arch to be cleaned.

Mention is also made of patent EP 108097 published on Jan. 20, 1988, which teaches a brushing device having a plurality of interchangeable modules, one of which has frustoconical brushes and another has three parallel-axis cylindrical brushes that are short and of large diameter, with the middle brush serving to brush the tops of teeth and with the assembly being received in a highly-enveloping case: nevertheless such a disposition is not very effective, firstly because the rotary motion of the middle brush opposes that of one of the side brushes thereby impeding proper effectiveness of the middle brush, and secondly because the presence of the middle brush determines a certain application height for the device which does not always enable action to be taken over the full height of teeth all the way to the gum.

In addition to the above-mentioned drawbacks, those known devices generally have constant separation between the brushes, which firstly requires several different heads or several different sizes of device to be proposed depending on the user (children, adults, . . . ), and secondly, even for a single user, does not enable uniform brushing effectiveness to be obtained on all teeth, given the differences in tooth thicknesses (molars, premolars, canines, . . . ); and in devices of the type described in patent CH 644256, which are the only devices enabling the brushes to be moved apart because they are mounted on flexible shafts and held at one end only, in addition to the above-mentioned drawback of controlling brushing direction, they do not enable uniform pressure to be applied to the teeth since the spacing between them cannot adapt itself to the width of teeth over their entire length, and such a disposition necessarily gives rise to bending and shear forces on the drive shafts which are damaged thereby in the long run.

In an attempt to resolve those difficulties, attention may be drawn to patent application FR 2 662 598 published on Dec. 6, 1991, which describes a tooth brushing device of the same type as that described in above-mentioned application FR 2 489 120 having two contra-rotating brushes on rigid shafts, that are free at their distal ends and that are held by their opposite ends via which they are driven: the case that receives them includes a guide in which one of the brush ends is movable away from the other over a circular arc guaranteeing continuity of drive around and by a gear wheel, with the help of a cable-and-spring contrivance; the object of that device is to adapt to teeth of any thickness and to maintain constant pressure thereon in substantially uniform manner over the full length of the brushes which, for that purpose, must remain substantially parallel throughout brushing. This also constitutes one of the objects of the present invention, but the solution taught by that prior document is very complex, is not reliable, and requires action to be taken by the user when the device is placed in the mouth, which tends to discourage use thereof and which means that good results are not guaranteed.

OBJECT AND SUMMARY OF THE INVENTION

The object of the device of the present invention is to satisfy all criteria for effective brushing and to remedy the drawbacks observed in known devices. It makes it possible to ensure that brushing always takes place in the ideal direction, without any need to verify and possibly reverse the operating direction, to clean both sides of the dental arch simultaneously, thereby significantly reducing brushing time, to enable the occlusal face to be brushed and then the vertical side faces of the dental arches without action being taken by the user, and regardless of the thickness of the teeth, and to enable this to be done at constant pressure and in a manner that is substantially uniform over the entire length of the brushes, with good clearance for evacuating away from the treated surface any particles that may be dislodged by the brushes, and with this being done by using a mechanical assembly that is simple, reliable, and of reasonable cost.

Such a mechanical toothbrush of the invention with a dual rotary brushing system comprises a handle-forming body and a head fixed on said handle, which head is provided with two adjacent contra-rotating brushes of cylindrical shape and having axes that are substantially parallel, and such that each of said two brushes is driven by a flexible shaft situated inside the head and supported, at least at its distal end by a respective bearing mounted on a support secured to the handle by any connection means that are independent of the brushes and that enables the two brushes to move apart one relative to the other, and then ensuring that they are urged towards each other by a return effect; said head thus includes either an open case or else arms enabling said supports to be carried and situated relative to the brushes on the side where the outer generator lines thereof move apart during rotation, thus leaving the opposite side completely free.

Said head is preferably interchangeable, being snap-fastenable to said handle, and in one embodiment, the two adjacent contra-rotating brushes are guided by bearings carried by two supports, each including two flexible blades or metal springs as described below.

Between the second support and the handle, which are normally fairly far apart from each other to allow the brushes to penetrate to the back teeth while the handle remains outside the mouth, said flexible shafts are preferably upwardly inclined, i.e. towards the back of the case or towards the support arms, which then leave a space in this portion that is open on at least three sides; naturally, this inclination can be provided without mechanical angle coupling means since the said shafts are flexible.

Said brushes are thus organized in such a manner as to begin by brushing the occlusal face and then, to enable the brushes to move apart so as to allow the teeth to pass between them while simultaneously brushing both vertical faces of the dental arches under substantially constant pressure, with said brushing always taking place in the direction going from the gum towards the ends of the teeth.

In a particular embodiment, the brushes are replaced by cylinders provided with rubber or elastomer fingers for the purpose of polishing the teeth by means of a suitable polish.

The result is a novel mechanical toothbrush having a dual rotary brushing system that counters the drawbacks of presently existing devices and enables the above-defined objects to be achieved, firstly by using elements already known in the prior art and in the public domain, and secondly by using elements that are specific, novel, and innovative, such as, in particular, driving the brushes by means of flexible shafts that are themselves held by one or more resilient and deformable supports making it possible both to move said brushes apart so as to adapt to any dentition and also to maintain constant pressure against said teeth during brushing, with this being done in as uniform a manner as possible over the entire length of the brushes and over the full the height of the teeth all the way to the gum itself, and in a manner that is very simple, that does not use a complex mechanism, and that even enables the brushes to be interchanged on their own without requiring the head assembly itself to be changed. Such a disposition makes it possible to separate clearly and thus to control properly the function of applying the brushes with constant pressure by means of their resilient supports, and the function of driving the brushes by means of the flexible shafts which not only cooperate with the supports to avoid impeding their function, but which also transmit torque from the motor without applying harmful forces to the drive system.

Furthermore, the flexibility and the optional inclination of the shafts between the handle and the brushes makes it possible to move the brushes down along the teeth, even over their inside faces, since the flexible shaft portion which then necessarily passes over teeth that are situated between those being brushed and the outside of the mouth can then pass over or between two spaced-apart teeth, deforming where necessary, and that is not possible with any presently known device.

In the present invention, there is no need to have a substantially closed protective case around the brushes, so while brushing the teeth it is possible simultaneously to brush the cheeks and the sides of the tongue. A substantially closed case is indeed useful, specifically for supporting fluid spray nozzles, and in this case the case nevertheless remains wide open in the space provided between the brushes and the handle so as to leave the flexible shafts free and allow them to pass over the teeth as mentioned above; depending on the characteristics of the invention, the bristles of the brushes may be of varying length and diameter, which makes it possible, in combination with the other characteristics of the invention, to clean the spaces between teeth by using bristles of sufficient length.

BRIEF DESCRIPTION OF THE DRAWINGS

Other advantages of the present invention could be mentioned, but those given above already suffice to demonstrate the novelty and the advantage thereof.

The description and the accompanying drawings are given by way of non-limiting example and relate to various embodiments of the invention.

MORE DETAILED DESCRIPTION

Figure 1:
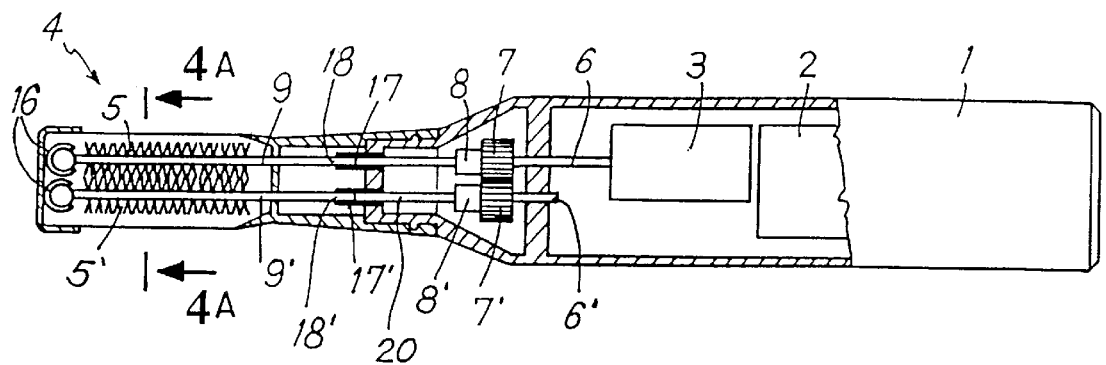
FIG. 1 is a fragmentary longitudinal section on taken line 1—1' of FIG. 2 through an entire brush, as seen from beneath or in front view.

The brush or device of the invention as shown in FIGS. 1 to 6 is constituted by a handle-forming hollow body 1 containing a transformer for an optional external power supply and/or an optionally-rechargeable battery 2 for powering a motor 3, together with a head 4 that may be disconnectable so as to be interchangeable, that snap-fastens on the body 1 and that is provided at its end with two adjacent rotary brushes 5, 5' of cylindrical shape and having substantially parallel axes.

The cross-sections of the body 1 and of the head 4 are preferably oval in shape, so as to make it easier to hold the device and to define its orientation within the mouth.

Figure 2:
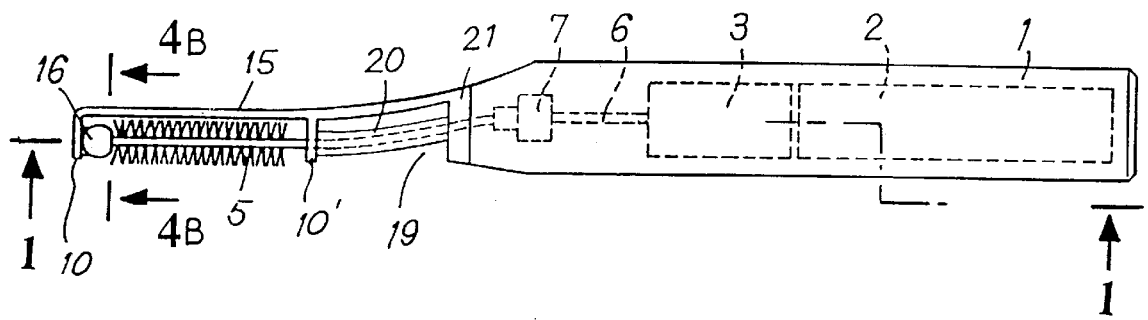
FIG. 2 shows a brush of the invention in side view, and is applicable both to the embodiment of FIG. 1 and to another embodiment described below with reference to FIG. 4B.
Figure 3:
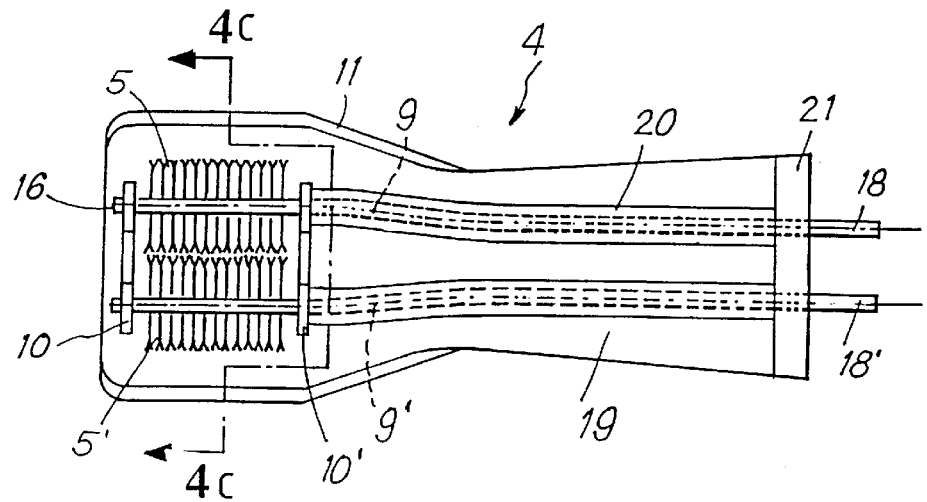
FIG. 3 is an enlarged front view of another embodiment of the head of the brush of the invention.

The motor 3 drives a first primary shaft 6 which in turn drives a second primary shaft 6' in the opposite direction by means of two gear wheels 7 and 7'. A friction clutch type torque limiter device associated with the gear wheels or with sleeves 17 described below may be included in order to avoid excessive force in the event of one of the brushes being jammed between two teeth, for example, so as to avoid damage to the teeth or to the drive system. Two female endpieces 8, 8' respectively secured to the two gear wheels 7, 7' transmit the rotary motion to two shafts that are flexible, at least in respective portions 9 and 9' situated inside the head 4 and that drive respective ones of the brushes 5 and 5'. These flexible shaft portions which are substantially parallel and which may be slightly inclined, both in the horizontal plane and in the vertical plane as shown in FIGS. 2 and 3, are terminated at their ends 18, 18' remote from the brushes 5, 5', i.e. their handle ends, by respective sleeves 17 in which they are engaged and with which they cooperate so as to be driven by the sleeves when the head is mounted on the body 1. The sleeves 17 and 17' may be secured to other shaft portions 20 that are themselves driven by the endpieces 8, 8' of the gear wheels 7, 7'. Depending on the embodiment, the sleeves 17, 17' and the female endpieces 8, 8' may coincide. As shown in FIGS. 2 and 3, the ends 18, 18' of shafts 9 and 9', which are then constituted by respective single flexible portions, may engage directly in the sleeves 8 when the head 4 is installed on the handle 1.

In the preferred embodiment shown in FIG. 2, where the axes of the shafts 9 and 9' are offset relative to the axis of the drive motor 3, each shaft is flexible along its entire length to its distal end to the point where it engages in one of the endpieces 8, 8' of the gear wheels 7, 7', with the shafts thus being constituted by respective single portions that do not include intermediate sleeves 17, 17', as also shown in FIG. 3. Under such circumstances, it is the flexibility of the shafts 9, 9' that accommodates the way the axes are offset in the space 19 which is open on at least three sides thereof so as to enable the brushes to reach as far as the back teeth, while the handle remains outside the mouth, as mentioned above.

Said flexible shafts between the second support 10' and the end 21 of the head 4 which co-operates with the sleeve 1 preferably pass inside respective fixed and likewise flexible sheaths 20 fixed at respective ends to said support 10' and to the end 21 of the head, thereby avoiding any risk of said rotating flexible shafts jamming between the teeth and damaging them.

The bristles of the brushes 5, 5' are implanted in rectilinear or helical manner. They are of varying length and diameter, in order to optimize brushing.

Figure 4A:
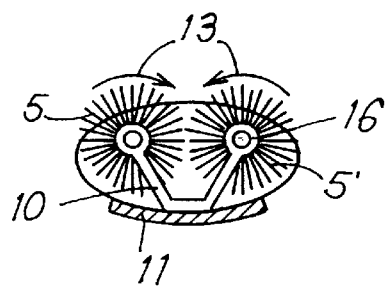
FIG. 4A is a section view on taken on line 4A—4A in of FIG. 1.
Figure 4B:
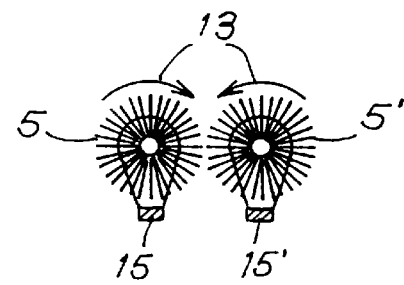
FIG. 4B is a section view on taken on line 4B—4B in FIG. 2.

Each of the flexible shafts 9, 9' is guided by at least one bearing 16 at its distal end, i.e. its end furthest from the handle or body 1. These bearings are mounted on a support 10 that enables the two brushes to move apart one relative to the other and then serves to urge the two brushes towards each other by a return effect that is due either to the resilience of a common support 10, as shown in FIGS. 4A or 4C for example, or else due to the resilience of the arms 15, 15' each carrying a support, as shown in FIG. 4B.

Figure 4C:
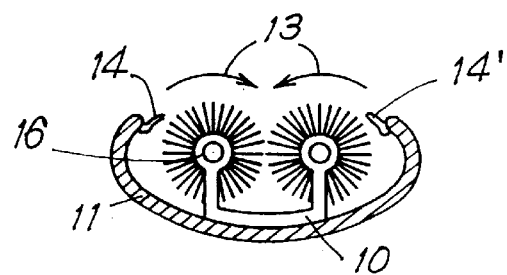
FIG. 4C is a section view taken on line 4C—4C in of FIG. 3.
Figure 5:
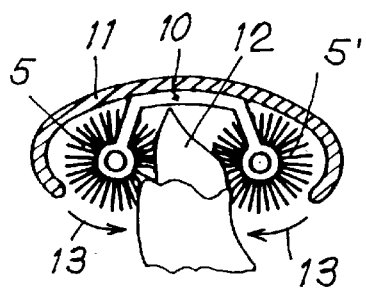
FIGS. 5 and 6 are cross-sections through a head showing the position of the brushes while in use, respectively on the bottom jaw and on the top jaw.
Figure 6:
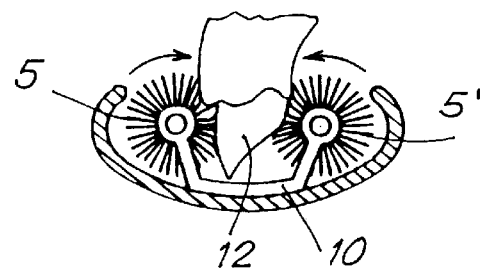

In the embodiment shown in FIGS. 2, 3, 4A, 4C, 5, and 6, said head 4 includes common supports 10, 10' that are U-shaped, suitable for being situated at opposite ends of the brushes 5, 5' inside a case 11 that is open to a greater or lesser extent, and extending the head 4. The case 11 may be made out of a material that is semirigid such as a plastic material that is deformable and flexible to some extent, which surrounds said brushes 5, 5' at least in part over that side where their outer generator lines move apart from one anther while the brushes are rotating, and is open at least on the opposite side. The case may nevertheless close up a little on said opposite side, as shown in FIGS. 4C, 5, and 6 so as to protect the mucous membranes and the tongue against the brushes; however as mentioned above, and as shown in FIG. 4A and to a greater extent in FIG. 4B, in preferred embodiments of the present invention, it can be desirable to achieve the opposite effect of brushing said mucous membranes and the tongue, so said case is, on the contrary, made as open as possible, while nevertheless always being present on the above-specified side so as to ensure that the device is always correctly presented to the teeth, i.e. in the proper brushing direction.

Both branches of each of the common supports 10 and 10' are constituted by flexible blades of plastic material that may be molded out of the same material as the connection means securing them to the handle independently of the brushes themselves, such as the above-described case 11 or the below-described arms 15, or they may be metal springs fixed to said connection means so as to enable the brushes to move apart and allow teeth 12 to pass between them, with the bases thereof being fixed to the inside of said case 11.

This feature constitutes one of the essential points of the invention. Teeth are cleaned by pressing the head of the device against the teeth in such a manner that the occlusal face is the first to be brushed, after which the teeth pass between the two brushes 5 and 5', urging them apart, with the directions of rotation of the flexible shafts 9 and 9' as shown in the figures by arrows 13 being such that brushing always takes place in a direction going from the gum towards the ends of the teeth, and without there being any need for a system that reverses the direction of rotation. The resilience of the flexible supports 10 and 10' is determined so that the pressure exerted by the brushes on the teeth is optimal, and the disposition of said supports 10 and 10', at least at their distal ends, and preferably at both ends of the brushes, enables said pressure to be maintained over the brushes as a whole so that they fit as well as possible to the shapes of the faces of the teeth to be brushed, due also to the resilience inherent to their drive shafts, with this amounting to the brushes being presented in substantially parallel manner providing the thickness of the teeth in the zone concerned is substantially constant.

For a case that is half-closed as shown in FIG. 4C, the brushing action may optionally be associated with nozzles 14 provided inside the head 4 for the purpose of spraying a liquid on the teeth 12, e.g. water containing bicarbonate.

In another embodiment, as shown in FIG. 4B, which is a section view on line 4B—4B in of FIG. 2, said head may include two deformable and resilient arms 15, 15' both situated, relative to the shafts 9, 9' of the brushes, on the side where the outer generator lines of the brushes move apart from one another during rotation, each of said arms carrying one of said supports 10 at its distal end. In this case, it is the arms themselves that enable the brushes to move one apart from the other and that urge them together again by a return effect, with the independent support 10 at the ends of said arms then possibly being rigid, serving merely to support the bearings 16.

In particular to enable the brushes 5, 5' to be removed and interchanged on their own without requiring said head 4 to be disconnected or changed, said bearings 16 supporting the distal ends of said brushes 5, 5' are in the form of hollow female sockets of ball-and-socket joints which co-operate with the ends of the said ends that are in the form of complementary balls that can be disconnected from said bearings 16. This particular form of bearing may be used in any of the embodiments shown in the accompanying figures, with the other ends 18 of the shafts 9, 9', adjacent to the handle 1 then being capable of engaging in the other support 10', when present, so as to subsequently to engage in said sleeves 17, or directly in the female endpieces 8 on the gear wheels 7, 7'.

As mentioned above, and in the preferred embodiments as shown in FIGS. 2 and 3, each of the shafts 9, 9' of said brushes 5, 5' is also supported adjacent to the body 1 or handle by at least one other bearing which is thus mounted on at least one second support 10'. This support may then be common to both brushes as in the embodiment using arms as shown in FIG. 4B. The support may be the same as that described for supporting the distal ends as explained above with reference to FIG. 3, and also to FIGS. 4A, 4C, et seq.

Heads 4 may also be provided in which the brushes 5, 5' are replaced by cylinders fitted with rubber or elastomer fingers for the purpose of polishing the teeth with the help of an appropriate polish.

What is claimed is:

1. A mechanical toothbrush having a dual rotary brushing system comprising:

a body defining a handle, a head secured on said handle, a brush assembly consisting of two, adjacent counter-rotating brushes in said head, said brushes being cylindrical and having axes substantially parallel to one another, flexible shafts respectively supporting said brushes, drive means connected to one end of each flexible shaft to drive said shaft and the respective brush supported thereon in rotation, each said flexible shaft having a distal end, said head including first supports rotatably supporting the distal ends of both flexible shafts, and further supports supporting said flexible shafts at locations spaced from said first supports, said first supports on said head being flexible to enable said flexible shafts to undergo flexing movement from an initial position in which said brushes are urged towards one another for contacting opposite surfaces of teeth being brushed to displaced positions to permit said brushes to move apart to accommodate teeth of varying thickness, the arrangement of said first supports and said flexible shafts causing the brushes to be urged towards one another to press against the opposite surfaces of the teeth being brushed as said brushes move up and down on said teeth.

2. A mechanical toothbrush according to claim 1, wherein said brushes have outer surfaces which, during rotation, move towards one another at one side of the brushes and away from one another at an opposite side of the brushes, said head including a case surrounding said brushes at the side at which the outer surfaces of the brushes move away from one another during rotation, said outer surface of the brushes being exposed at the other side of the brushes at which the surfaces move towards one another during rotation, a U-shaped support member having a base fixed to said case and two flexible branches extending from said base and constituting said first supports for the distal ends of said flexible shafts, and bearings on said flexible branches rotatably supporting respective distal ends of said flexible shafts.

3. A mechanical toothbrush according to claim 1, wherein said brushes have outer surfaces which, during rotation, move towards one another at one side of the brushes and away from one another at an opposite side of the brushes, said head including a case surrounding said brushes at the side at which the outer surfaces of the brushes move away from one another during rotation, said outer surface of the brushes being exposed at the other side of the brushes at which the surfaces move towards one another during rotation, said first supports comprising two deformable and resilient arms on said head situated on the side of said brushes which move away from one another during rotation of the brushes, and a bearing on each arm at a distal end thereof supporting the distal ends of the flexible shafts.

4. A mechanical toothbrush according to claim 1, wherein the bearings supporting the distal ends of the flexible shafts each comprises a ball and socket joint including a hollow female socket and a ball engaged in said socket.

5. A mechanical toothbrush according to claims 4, wherein the ball and socket of each said ball and socket joint are separable from one another.

6. A mechanical toothbrush according to claim 5, wherein the balls of the ball and socket joints are secured to the distal ends of said flexible shafts and the sockets are secured to said first supports.

7. A mechanical toothbrush according to claim 1 wherein said flexible shafts include portions which are inclined relative to one another.

8. A mechanical toothbrush according to claim 1, wherein said shafts include portions in said head which are inclined relative to the axes of said cylindrical brushes.

9. A mechanical toothbrush according to claim 1, wherein the brushes have bristles of varying lengths and diameters.

10. A mechanical toothbrush according to claim 1, wherein the head includes nozzles enabling a liquid to be sprayed on the teeth.

11. A mechanical toothbrush according to claim 1, wherein the first supports which are flexible urge the brushes resiliently towards one another with a predetermined pressure.

12. A mechanical toothbrush according to claims 1, wherein the flexible shafts terminate at said one ends by respective endpieces, sleeves engaged with said endpieces and at least two gear wheels connected to said sleeves and driven by said drive means, said drive means including a motor in said handle, said head being mounted on said handle and being disconnectable therefrom.

\* \* \* \* \*